United States Patent [19]
Stoffelen

[11] Patent Number: 4,601,200
[45] Date of Patent: Jul. 22, 1986

[54] MEASURING APPARATUS

[75] Inventor: Eduardus Stoffelen, Brasschaat, Belgium

[73] Assignee: Elektriciteit voor Goederenbehandeling Marine en Industrie, in het verkort: "Egemin", naamloze vennootschap, Schoten, Belgium

[21] Appl. No.: 499,518

[22] Filed: May 31, 1983

[30] Foreign Application Priority Data

Jun. 7, 1982 [LU] Luxembourg .............................. 84185

[51] Int. Cl.⁴ ........................ G01F 23/28; G01N 9/00; G01N 11/16
[52] U.S. Cl. ..................................... 73/290 V; 73/291; 73/54; 73/59; 73/32 A; 73/862.41; 374/142
[58] Field of Search ...................... 374/6, 14, 117, 142; 73/290 V, 291, 32 A, 309, 321, 59, 54, 437, 10, 64, 836, 862.39, 862.41; 33/126, 126.5, 126.4 R, 126.4 A

[56] References Cited

U.S. PATENT DOCUMENTS

| | | | |
|---|---|---|---|
| 1,447,185 | 3/1923 | Sammet | 73/836 |
| 1,893,749 | 1/1933 | Klopsteg | 73/59 |
| 2,033,964 | 3/1936 | Wazau | 73/836 |
| 2,239,726 | 4/1941 | Martin | 73/59 |
| 2,883,855 | 4/1959 | Spengler et al. | 73/64 |
| 3,206,979 | 9/1965 | Banks | 73/290 V |
| 3,208,281 | 9/1965 | Kalmus et al. | 73/290 V |
| 3,372,592 | 3/1968 | Gravert | 73/290 V |
| 3,796,088 | 3/1974 | Gustafsson et al. | 73/59 |
| 4,000,653 | 1/1977 | Booth et al. | 374/141 |
| 4,170,311 | 10/1979 | Spaw | 73/290 V |
| 4,219,133 | 8/1980 | Sinsky | 222/39 |

FOREIGN PATENT DOCUMENTS

| | | |
|---|---|---|
| 1498556 | 4/1969 | Fed. Rep. of Germany . |
| 2012475 | 12/1971 | Fed. Rep. of Germany . |
| 2250120 | 5/1974 | Fed. Rep. of Germany . |
| 2800938 | 6/1978 | Fed. Rep. of Germany ........ 73/835 |
| 102467 | 12/1973 | German Democratic Rep. . |

Primary Examiner—Charles Frankfort
Assistant Examiner—Thomas B. Will
Attorney, Agent, or Firm—Schwartz, Jeffery, Schwaab, Mack, Blumenthal & Evans

[57] ABSTRACT

A measuring apparatus, including a measuring device; a measuring element secured at one of its ends to the measuring device; a measuring body secured on the free end of the measuring element; a pendulum capable of oscillating the measuring element; a positioning motor for actuating the measuring device; and a logic control unit actuating the pendulum.

26 Claims, 5 Drawing Figures

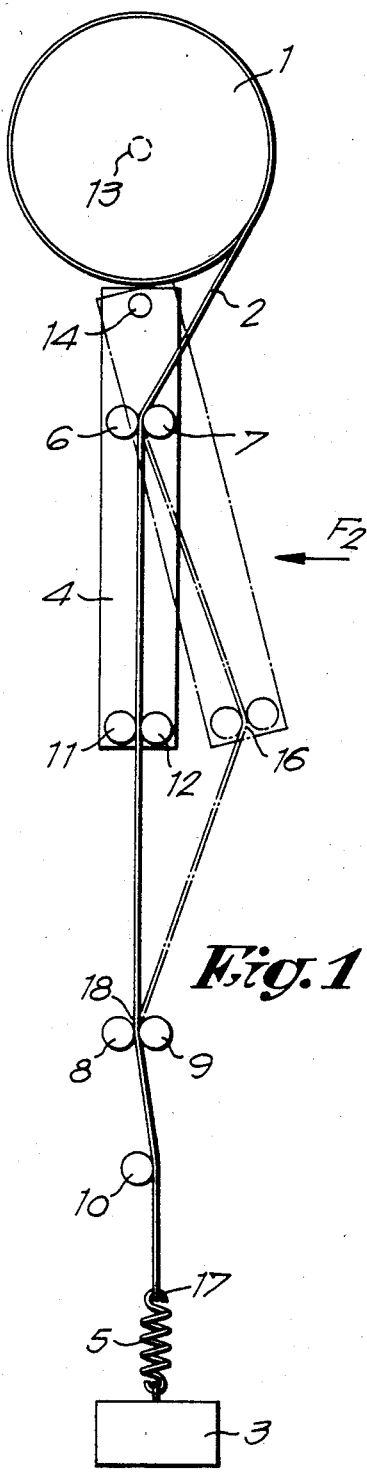
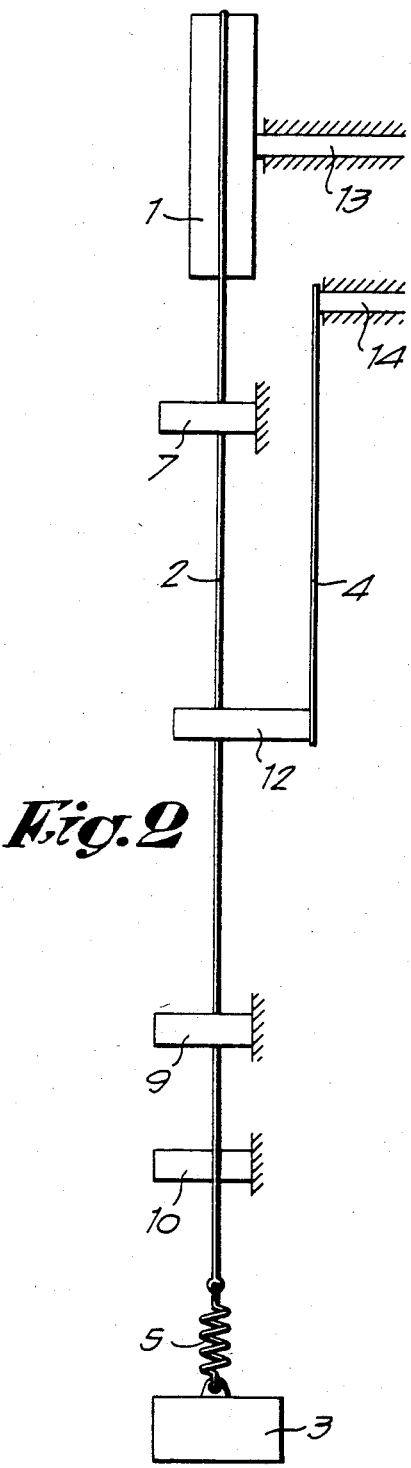
Fig.1
Fig.2

MEASURING APPARATUS

SUMMARY OF THE INVENTION

This invention relates to a measuring apparatus, more particularly to an apparatus allowing dynamic measurement of the properties of a liquid such as the amount, the density, the viscosity and, if desired, the temperature.

More particularly, the invention permits: measuring liquid levels with respect to one or several index marks; measuring density separation surfaces in the liquids and determining said surfaces with respect to one or several index marks; measuring densities of liquids at various levels; measuring viscosities of liquids at various levels; measuring temperatures of liquids at various levels; and measuring the vertical dimensions of the liquid container or the liquid channels, as well as the height differences with respect to the liquid levels and/or the density separation surfaces.

The apparatus according to the invention will be advantageously used in any kind of liquid containers or channels, more particularly when vapours and/or gases likely to form an explosion danger and against which preventive steps must be taken, may exist or can occur, momentarily or permanently above the liquid, as well as when storing liquids and/or gases the pressure of which is higher than atmospheric pressure.

For this purpose, the apparatus according to the invention allowing the above-mentioned measurements and still others uses a principle known per se, namely the measurement of the tension created in a cable, a rope or similar by means of oscillations induced in the said cable or rope.

The advantages obtained with the apparatus according to the invention are namely as follows:

it allows completely separating the inside of the liquid container from the atmosphere and possible electric control elements;

it avoids electrical signals in the dangerous area above the liquid level and/or in the overpressure area;

it may be installed and/or removed without extracting dangerous products, if any, from the container;

even when it is first installed, it allows independent determination of the vertical dimensions of the liquid container as well as the absolute height difference of the liquid or the density separation surfaces with respect to the container, while indicating said differences in an arbitrary unit, e.g. in millimeters or fractions of millimeters.

The apparatus according to the invention which is namely capable of meeting the above mentioned requirements, comprises substantially the combination of a measuring device; a measuring element secured at one of its ends to the said measuring device; a measuring body secured on the free end of the said measuring element; a pendulum capable of oscillating the said measuring element; means for actuating the said measuring device; means for actuating the said pendulum; and a logic control unit.

BRIEF DESCRIPTION OF THE DRAWINGS

The features of the present invention will be more clearly apparent from the following description of a preferred embodiment given by way of example, without any limitation, reference being made to the enclosed drawings in which:

FIG. 1 is a diagrammatic vertical section of an apparatus according to the invention;

FIG. 2 shows a view according to the arrow F2 of FIG. 1;

DETAILED DESCRIPTION OF THE INVENTION

Figure 3:
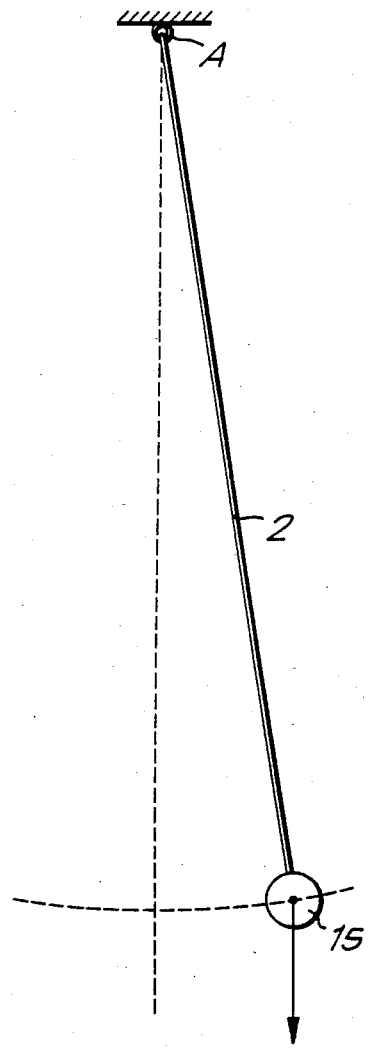
FIG. 3 is a diagrammatic view of a simple pendulum.

As shown in FIGS. 1 and 2, the apparatus according to the invention comprises a drum or measuring device 1, a strand, a rope, a tape, a cable or similar support member 2, a body 3, a pendulum 4 and a mechanical filter 5.

The strand 2 is guided between two pairs of stationary guides 6-7 and 8-9, a stationary guide 10 and two moving guides 11-12 secured on the pendulum 4.

The drum 1 is dimensioned so that it may receive a strand amount allowing the shifting of the body 3 along the whole measuring height. It may be provided with a helical groove in order to obtain a high degree of accuracy.

Needless to say the relation between the rotation of the drum 1 and the vertical shifting of the body 3 must be known with a very high degree of accuracy, it being possible to drive the drum in any manner, e.g. through to a step motor, a permanent magnet driven into rotation by electromechanical oscillations, or a similar manner.

The strand 2 must be sufficiently thin and flexible to remain tight under the influence of the minimum force being detected, which is the case, e.g., when detecting the lower bottom of a liquid container. It must be also sufficiently strong to resist the maximum force being detected, which is the case, e.g. when detecting the upper bottom of the container. The strand 2 must be capable of blocking the winding system without being distorted or broken.

The aimed accuracy determines the admissible elongation of the strand under a mechanical load, as well as the admissible expansion of the strand under the influence of the room temperature.

The body 3 will have preferably a cylindrical shape. It is made of a material the specific weight of which is such that, when the body 3 is immersed in a liquid the density of which is the highest one being provided, the latter subjects the strand to a force which is sufficiently high to maintain the strand 2 in a taught state.

The body 3 will be finished so that, when it is removed from the liquid, it carries away the minimum amount of liquid.

The pendulum 4, which allows the conversion of the tension in the strand 2 into a measuring signal, will be brought to its rest position through the strand 2 with a force which is a function of the weight with which the strand is loaded, i.e. the apparent weight of the body 3.

The oscillation of the pendulum 4 is measured and transmitted to a logic control unit which is also capable of recording and analyzing the resonance signals of the pendulum 4.

In a preferred embodiment, the oscillation of the pendulum is obtained through a permanent magnet (not shown in the drawings) secured on the axis 14 and capable of being actuated through an electromagnet connected with the logic control unit.

The logic control unit could consist of a microprocessor controlling both the position of the body 3 and the oscillation of the pendulum 4 and analyzing the resonance signals of the pendulum 4. Such a control unit can make measuring results available to each concerned person and it is capable of receiving controls and possibly parameters valuable for the system.

The purpose of the mechanical filter 5 is to prevent acceleration forces in the strand 2 resulting from oscillations of the pendulum 4 from acting on the body 3.

The resonance frequency of the elements 3–5 must be suitably damped so that it does not influence the function of the pendulum and it must be outside the frequency band which is axially generated by the pendulum 4 in the strand 2. The mechanical filter may be made of any resilient material such as an artificial or synthetic resin, a spring or a similar device.

Before describing the functioning of the apparatus according to the invention, it seems judicious to start from the pendulum according to FIG. 3 for our description.

As regards a pendulum such as shown in FIG. 3, it is known that the frequency thereof is given by the formula:

$$f = \frac{1}{2\pi} \sqrt{\frac{\mu}{J} - \frac{\lambda^2}{4J^2}}$$

wherein:
f = the frequency;
$\mu$ = a constant determining for the torque about A;
$\lambda$ = friction constant;
J = inertia moment of the pendulum;
A = suspension point.
In this example:
$\mu = mgl$
$J = ml^2$
m = the mass of the object 15 secured to the pendulum (the mass proper of the pendulum is neglected);.
g = gravitation constant;
l = the length of the pendulum.
Considering that the friction in the point A and the air resistance are being neglected, $\lambda$ will be zero.

Accordingly, the above formula becomes:

$$f = \frac{1}{2\pi} \sqrt{\frac{g}{l}}$$

From the foregoing, it results that, J and $\lambda$ being invariable, the frequency is determined by $\mu$, i.e. the return torque.

According to the invention and as shown in FIG. 1, the pendulum 4 is provided with a measuring body 3 which will influence the said return torque and, accordingly, the frequency.

In that case:
$\mu$ = constant determining for the return torque about 14, which is itself determined by the weight of the pendulum 4; the weight of the body 3 and the weight of the strand portion situated between the points 16 and 17;
J = inertia moment of all the elements participating to the oscillation about the axis 14;
$\lambda$ = friction, about the axis 14, of all the elements participating to the oscillation.

In the apparatus according to the invention, it is given that the weight of the strand, the weight of the pendulum and the friction in the points 16 and 18 are neglected, which means that $\lambda$ and J are constants independently from the unwound strand length, whereas $\mu$ is determined by the weight of the body 3.

The apparatus according to the invention allows to measure various properties of a liquid and it operates as described hereafter.

In order to measure the level of a liquid, use is made of the fact that the oscillation frequency of the pendulum 4 is determined by the weight of the body 3. In fact, when said body 3 is immersed in a liquid, the apparent weight is lowered, thereby reducing the said frequency.

It is apparent that the immersion of the body 3, e.g. down to the half height of the latter into a liquid corresponds to a determined frequency, e.g. fr which may be selected as a reference frequency.

It results that the measurement of a liquid level requires an adjusting system which may change the position of the body 3 until the pendulum oscillates at a frequency fr. When the axis 13 is controlled by a step motor, this means that the number of steps of the motor in the same direction determines the height difference relative to a reference position.

In order to measure a liquid level situated between two liquids, like in the previous example, it is sufficient to select a predetermined frequency value fr, to inform the said logic control unit about this value and to measure the height difference relative to a reference point.

Figure 4:
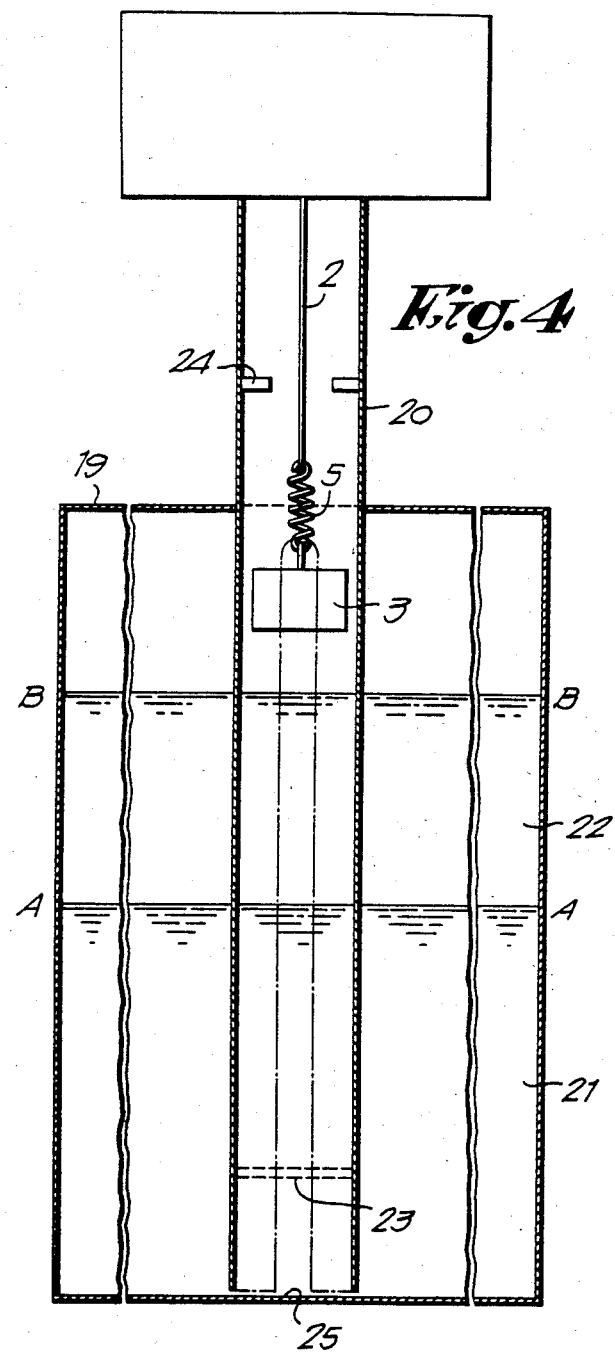
FIG. 4 shows an application of the apparatus according to the invention.

A current application of a measuring apparatus according to the invention is shown in FIG. 4.

This figure shows a vessel 19 provided with an apparatus according to the invention which, in this example, is mounted on the upper end of a tube 20. The latter is preferably extended into the vessel 19 in order to form a guiding means for the body 3. The inside of said tube 20 permanently communicates with the content of the vessel, e.g. by means of a slit provided on the whole height of the container 19. The said content consists namely of two liquids 21, 22 respectively having different densities the levels of which are situated on the lines A—A and B—B.

The said tube 20 comprises preferably two stops 23–24 respectively used as reference points. However, said stops are not necessary because the bottom 25 of the vessel and the lower portion of the apparatus according to the invention may also function as stops.

In order to determine the upper index point, it is sufficient to shift the body 3 upwardly against the stop 24.

Owing to said contact, the tension of the spring 5 increases and the weight of the body 3 apparently increases too, thereby resulting in an increase of the resonance frequency. Thus, the value frl of said frequency corresponds to that position of the body 3 and it is sufficient to inform the adjusting system (microprocessor) about this value. Accordingly, said reference point corresponds to a height difference of zero.

The determination of the lower index point (stop 23 or bottom 25) is carried out in the same manner, except that the contact of the body 3 with the stop 23 or the bottom 25 causes an apparent decrease of the weight of the body 3 and, accordingly, a reduction of the resonance frequency. This frequency which is communicated to the adjusting system, corresponds to a maximum height difference.

Considering the fact that the apparent weight of a body depends on the density of the liquid into which it is immerged, it is sufficient to situate successively the body 3 under the levels B—B and A—A in order to be able to determine the density of the liquids 22 and 21 starting from the resonance signals transmitted to the adjusting system.

In the same manner, it is possible to measure the viscosity of the liquid. In fact, it is known that the friction of the liquid on the body 3 during its travel at a constant speed through the liquid is proportional to the viscosity. This viscosity may be determined starting from the apparent increase or decrease of the weight of the body 3 and the increase or the decrease of the frequency of the pendulum 4.

The apparatus according to the invention allows also to measure the temperature in a liquid.

Figure 5:
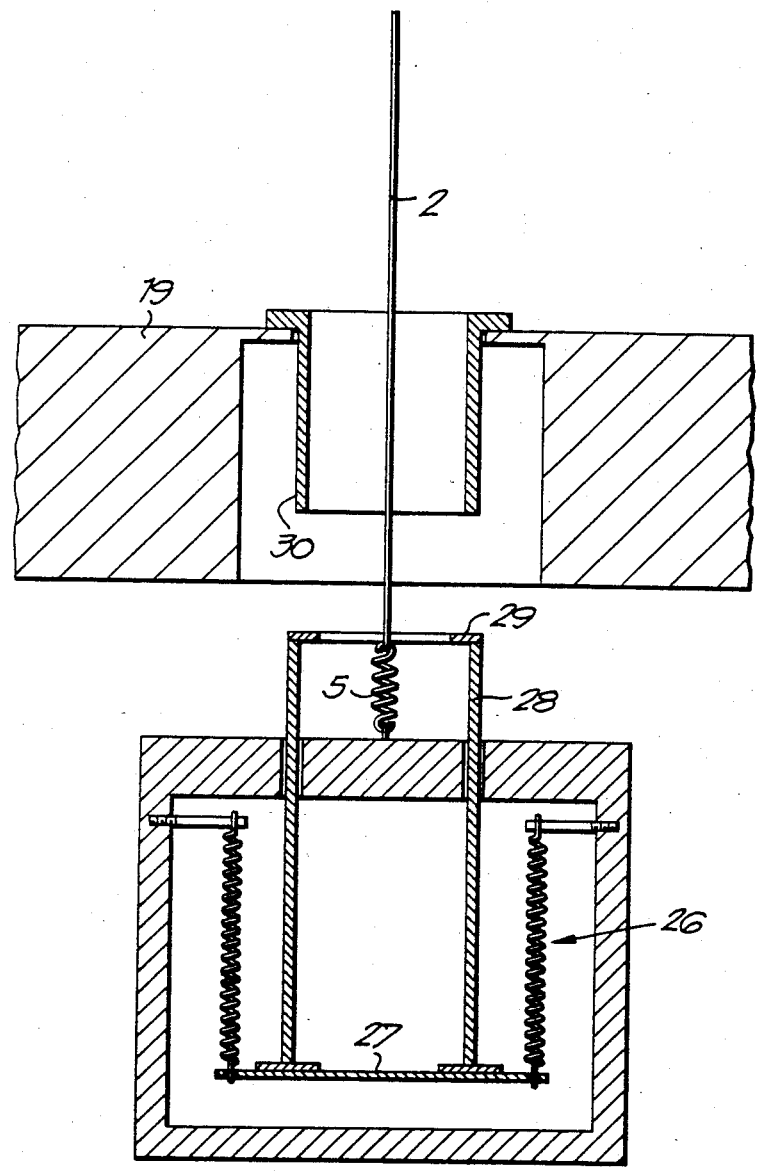
FIG. 5 shows a modified embodiment allowing the measurement of the temperature of a liquid.

For this purpose and as shown in FIG. 5, the body 3 will be provided with a temperature sensor 26 interconnected, through one of its ends, with the body 3, the other end 27 of said sensor being free. The shifting of the end 27 relative to the body 3 gives an indication of the temperature in and/or about the body 3.

The above-mentioned free end 27 is provided with rods 28 connected, outside the body 3, through a ring 29 forming a stop. The arrangement is completed by an element 30 bearing freely on the stop 24.

When the body 3 is shifted upwardly, at a certain point, the ring 29 contacts the element 30 and raises it, thereby inducing a frequency change in the pendulum 4, so that it is possible to perfectly know the position of the body 3 for a given temperature.

It results that a temperature variation of the sensor 26 brings the ring 29 against the element 30 in another position of the body 3.

Owing to the small amplitude of the pendulum and the negligible friction in the guiding means of the strand, the latter may be shifted slowly without disturbing the measurement.

In addition, it is to be noted that the control of the strand is positive, i.e. the oscillation of the strand 2 is obtained through the pendulum 4 which moves the strand 2 in a well determined plane. It results that the unwanted movements of the strand 2 in other planes are excluded, thereby providing a very accurate measurement.

Owing to the presence of the guiding means 10, the unwanted oscillations of the point 17 are still damped.

It is still to be noted that the non-linearity of the pendulum is treated through the elements 3 and 5.

In fact, the height variation of the point 17 is the square of that of the angular amplitude of the pendulum 4, thereby causing substantial accelerations of said point 17.

In order to prevent said accelerations from influencing the measurement, the body 3 is interconnected with the strand 2 through the intermediary of the spring 5 damping out said accelerations.

This spring 5 must be designed so that the frequency of the elements 3 and 5 is higher than the double highest frequency of the pendulum.

Thus $$\frac{1}{2\pi}\sqrt{\frac{k}{m}} > \frac{1}{2\pi}\sqrt{\frac{\mu}{J} - \frac{\lambda^2}{4J^2}}$$

wherein k is a constant of the spring.

In addition, this frequency of the elements 3 and 5 must be situated outside the frequency spectrum of the pendulum in order to prevent the resonance of the body 3 on the pendulum frequency or on a harmonic of said frequency.

Needless to say, the invention is not at all limited to the above-described embodiment as shown in the enclosed drawings. Any alterations may be brought thereto without departing from the scope of the invention.

I claim:

1. Measuring apparatus, comprising:
    a measuring device;
    a measuring element secured at a first end to said measuring device;
    a measuring body secured to a second free end of said measuring element;
    a pendulum means capable of modulating oscillations of said measuring element, said pendulum means being responsive to a tension in said measuring element induced by said measuring body;
    means for actuating said measuring device;
    means for actuating said pendulum; and
    means for interpreting the oscillations of said measuring element.

2. Apparatus according to claim 1, wherein said measuring device comprises a drum.

3. Apparatus according to claim 1, wherein said measuring element consists of a flexible element.

4. Apparatus according to claim 1, wherein the free end of said measuring element is connected to said measuring body through a mechanical filter means.

5. Apparatus according to claim 4, wherein said mechanical filter means is comprised of a resilient material.

6. Apparatus according to claim 5, wherein said mechanical filter means comprises a spring means.

7. Apparatus according to claim 5, wherein said resilient material is a synethetic resin.

8. Apparatus according to claim 3, wherein said measuring element is guided on at least two levels, a first point of said pendulum means on said measuring element being situated between said guiding levels.

9. Apparatus according to claim 8, wherein said guiding levels and said leading point are situated in a common vertical plane when said pendulum means is at rest.

10. Apparatus according to claim 8, wherein said guiding levels and said first point are situated in different vertical planes when said pendulum means is at rest.

11. Apparatus according to claim 8, wherein said guiding levels, said first point and an oscillation axis of said pendulum means are situated in a common vertical plane when said pendulum means is at rest.

12. Apparatus according to claim 8, wherein said guiding levels, said first point and an oscillation axis of said pendulum means are situated in different vertical planes when said pendulum means is at rest.

13. Apparatus according to claim 8, wherein said guiding levels, said first point, an oscillation axis of said pendulum means and the axis of said measuring device are situated in a common vertical plane when said pendulum means is at rest.

14. Apparatus according to claim 8, wherein said guiding levels, said first point, an oscillation axis of said pendulum means and the axis of the said measuring device are situated in different vertical planes when said pendulum means is at rest.

15. Apparatus according to claim 1, wherein said measuring element is complementarily guided under a pair of guiding levels, by a guiding means situated outside of a vertical plane passing through said pair of guiding levels.

16. Apparatus according to claim 1, wherein a first point of said pendulum and a guiding means situated above and under said first point comprise two guiding elements, situated on both sides of the said measuring element.

17. Apparatus according to claim 2, wherein said drum is driven by a step motor.

18. Apparatus according to claim 1, wherein said pendulum means is actuated by a magnet.

19. Apparatus according to claim 1, wherein said measuring element oscillates at a frequency responsive to the tension in said measuring element.

20. Apparatus according to claim 16, wherein said guiding elements are cylinders.

21. Measuring apparatus, comprising:
- a measuring device, said measuring device comprising a drum driven through a positioning motor;
- a measuring element, consisting of one flexible element, taken from the group consisting of a strand, a rope, a cable, and a tape;
- a measuring body secured on a free end of said measuring element;
- a pendulum means capable of oscillating said measuring element;
- means for actuating said pendulum means;
- and a means for interpreting oscillation of said measuring element;
- all of the above elements, except for said measuring body and a part of said measuring element, being located outside a vessel containing a material to be measured.

22. An apparatus for measuring physical properties of a fluid comprising:
- a strand, disposed vertically, having an upper end, a lower end, and a portion intermediate of said upper end and said lower end;
- means, mechanically coupled to said lower end of said strand and adapted to be immersed in said fluid, for applying a tension to said strand dependent at least in part on physical properties of said fluid;
- means, mechanically coupled to said upper end of said strand, for positioning vertically said tension applying means; and
- pendulum means, mechanically coupled to said intermediate portion of said strand, for horizontally displacing a part of said intermediate portion, and thereafter for oscillating with a frequency dependent on said tension applied to said strand.

23. An apparatus as claimed in claim 22, further comprising:
- first restraining means, mechanically coupled to said strand between said upper end and said lower end for restraining horizontal motion of a first portion of said strand and horizontally adjacent said first restraining means; and
- second restraining means, mechanically coupled to said strand between said first restraining means and said lower end, for restraining horizontal motion of a second portion of said strand horizontally adjacent to said second restraining means, said first portion and said second portion of said strand defining there between said intermediate portion of said strand.

24. An apparatus as claimed in claim 22, further comprising means, interposed between said lower end of said strand and said means for applying tension, for mechanically filtering oscillations in a predetermined frequency range.

25. A method of measuring characteristics of a fluid comprising the steps of:
- (a) submerging, into the fluid, a measuring body suspended from a measuring element capable of modulating the oscillation of a pendulum means in response to a force exerted on said measuring element by said measuring body;
- (b) sensing the oscillation frequency of said pendulum means;
- (c) adjusting the vertical position of said measuring body until the pendulum means oscillates at a predetermined frequency, said predetermined frequency corresponding to a predetermined vertical reference position;
- (d) determining the difference between the actual position of the measuring body and the predetermined reference position; and
- (e) calculating desired characteristics of the fluid, based upon said difference.

26. The method of claim 25, wherein the step of adjusting the vertical position is controlled by a step motor.

* * * * *